(12) United States Patent
Pan et al.

(10) Patent No.: US 9,260,474 B2
(45) Date of Patent: Feb. 16, 2016

(54) METHOD FOR SOLID PHASE SYNTHESIS OF LIRAGLUTIDE

(75) Inventors: Junfeng Pan, Guangdong (CN); Jian Liu, Guangdong (CN); Yaping Ma, Guangdong (CN); Jiancheng Yuan, Guangdong (CN)

(73) Assignee: HYBIO PHARMACEUTICAL CO., LTD., Shenzhen, Guangdong (CN)

( * ) Notice: Subject to any disclaimer, the term of this patent is extended or adjusted under 35 U.S.C. 154(b) by 29 days.

(21) Appl. No.: 14/344,660

(22) PCT Filed: Aug. 30, 2012

(86) PCT No.: PCT/CN2012/080756
§ 371 (c)(1),
(2), (4) Date: Mar. 13, 2014

(87) PCT Pub. No.: WO2013/037266
PCT Pub. Date: Mar. 21, 2013

(65) Prior Publication Data
US 2014/0350219 A1    Nov. 27, 2014

(30) Foreign Application Priority Data

Sep. 14, 2011    (CN) .......................... 2011 1 0271342

(51) Int. Cl.
*C07K 1/20* (2006.01)
*C07K 14/575* (2006.01)
(Continued)

(52) U.S. Cl.
CPC ................ *C07K 1/042* (2013.01); *C07K 1/064* (2013.01); *C07K 1/1077* (2013.01); *C07K 1/14* (2013.01); *C07K 14/605* (2013.01)

(58) Field of Classification Search
None
See application file for complete search history.

(56) References Cited

U.S. PATENT DOCUMENTS 6,268,343 B1    7/2001  Knudsen et al.
6,458,924 B2    10/2002 Knudsen et al.
(Continued)

FOREIGN PATENT DOCUMENTS

CN    1350548      5/2002
CN    101555272    10/2009
(Continued)

OTHER PUBLICATIONS

Madsen et al. Structure-Activity and Protraction Relationship of Long-Acting Glucagon-like Peptide-1 Derivatives . . . Journal of Medicinal Chemistry. 2007, vol. 50, No. 24, pp. 6126-6132.*
(Continued)

*Primary Examiner* — Jeffrey E Russel
(74) *Attorney, Agent, or Firm* — Merchant & Gould P.C.

(57) ABSTRACT

Provided is a method for solid phase synthesis of liraglutide, comprising the following steps: A), Fmoc-Gly-resin being obtained by coupling resin solid phase carrier with glycine with N-end protected by Fmoc(Fmoc-Gly-OH) in the presence of activator system; B) according to the peptide sequence of the main chain of liraglutide, successively coupling with amino acids with N-ends protected by Fmoc and protected side chains by the method for solid phase synthesis, wherein lysine employs Fmoc-Lys(Alloc)-OH; C) removing the protective group, Alloc, from the side chain of lysine; D) coupling the side chain of lysine with Palmitoyl-Glu-OtBu by the method for solid phase synthesis; E) cleavage, removing protection groups and resin to obtain crude liraglutide; F) purifying and lyophilizing to obtain liraglutide.

6 Claims, 1 Drawing Sheet

(51) Int. Cl.
*C07K 1/04* (2006.01)
*C07K 1/107* (2006.01)
*C07K 1/06* (2006.01)
*C07K 14/605* (2006.01)
*C07K 1/14* (2006.01)

(56) References Cited

U.S. PATENT DOCUMENTS

| | | | |
|---|---|---|---|
| 6,514,500 B1* | 2/2003 | Bridon et al. | 424/193.1 |
| 7,235,627 B2 | 6/2007 | Knudson et al. | |
| 7,612,166 B2* | 11/2009 | Kumar et al. | 530/344 |
| 2002/0068695 A1* | 6/2002 | Scolastico et al. | 514/9 |
| 2009/0239805 A1* | 9/2009 | Tregear et al. | 514/13 |
| 2010/0015173 A1* | 1/2010 | Boato et al. | 424/193.1 |
| 2011/0318373 A1* | 12/2011 | Sasikumar et al. | 424/185.1 |

FOREIGN PATENT DOCUMENTS

| | | |
|---|---|---|
| CN | 102286092 | 12/2011 |
| CN | 102584982 A * | 7/2012 |
| EP | 1180121 A1 | 2/2002 |
| EP | 2813514 A1 | 12/2014 |
| WO | WO 99/43705 | 9/1999 |
| WO | WO 2004/011498 | 2/2004 |

OTHER PUBLICATIONS

European Search Report dated Mar. 13, 2015 for European Patent Application No. 12 83 1927.

Jiang et al.: "Development of Orthogonal Protection of Lysine in Fmoc-Based Strategy Peptide Synthesis", Journal of Chongqing University of Technology (Natural Science), vol. 25, No. 4, Apr. 15, 2011, pp. 23-27, 32, XP008173214, ISSN: 16711-0924.

Chang-bing Li, "Research on Fmoc Chemistry Solid Phase Synthesis of Difficult Peptide AM-55", 2007. (English Abstract).

He et al., "Development of Orthogonal Protection of Lysine in Fmoc-Based Strategy Peptide Synthesis", *Journal of Chongqing University of Technology* (*Natural Science*), vol. 25, No. 4, 2011, pp. 23-27 (English Abstract Provided).

International Search Report for International Application No. PCT/CN2012/080756 mailed Dec. 6, 2012.

* cited by examiner

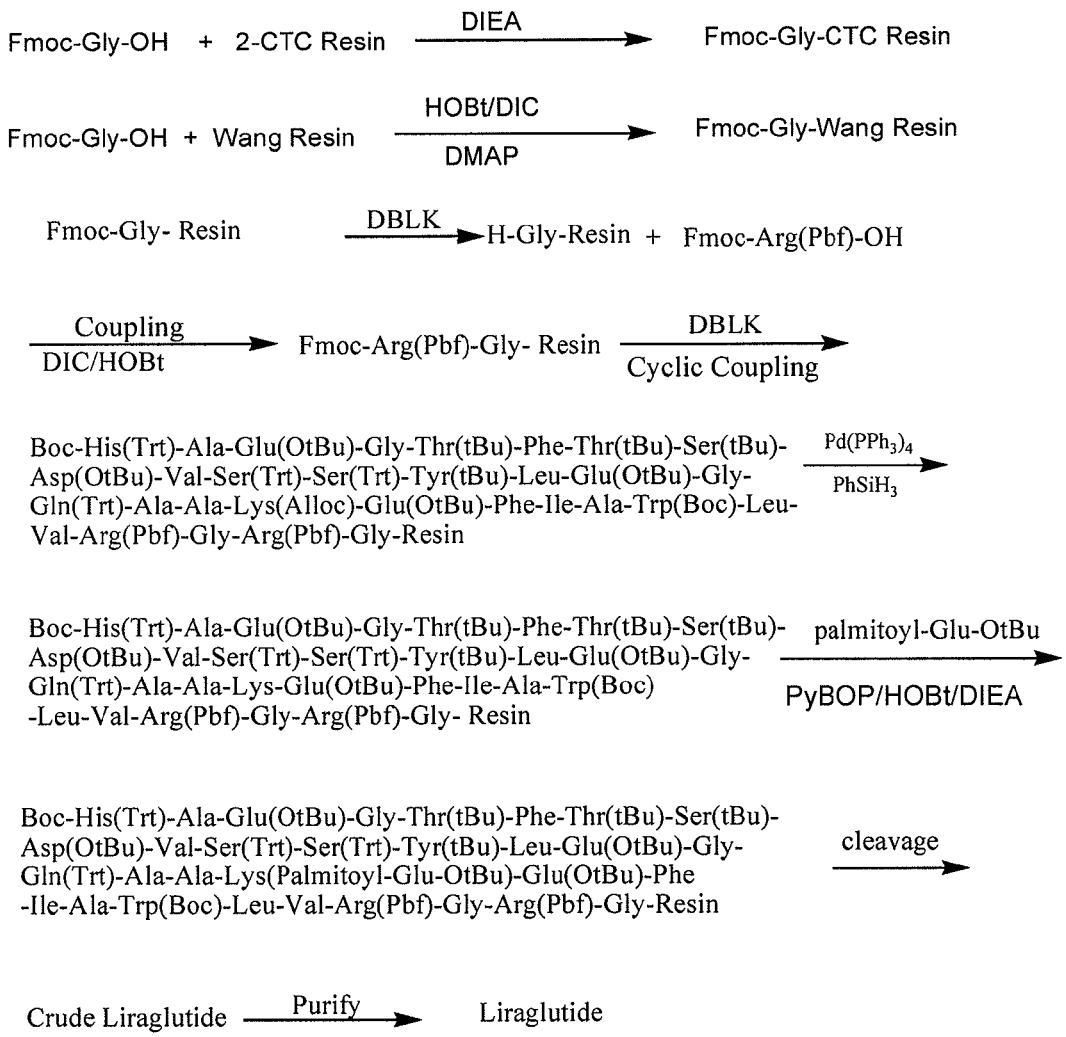

US 9,260,474 B2

METHOD FOR SOLID PHASE SYNTHESIS OF LIRAGLUTIDE

The present application is a National Stage Application of PCT/CN2012/080756, filed Aug. 30, 2012, which claims the priority of Chinese application No. 201110271342.3, filed on Sep. 14, 2011 and which applications are incorporated herein by reference. To the extent appropriate, a claim of priority is made to each of the above disclosed applications.

FIELD OF THE INVENTION

The present invention relates to a synthesis method for polypeptides, and particularly to a method for solid phase synthesis of liraglutide.

BACKGROUND OF THE INVENTION

Liraglutide has the following sequence: H-His-Ala-Glu-Gly-Thr-Phe-Thr-Ser-Asp-Val-Ser-Ser-Tyr-Leu-Glu-Gly-Gln-Ala-Ala-Lys(N-ε-(N-α-Palmitoyl-L-γ-glutamyl))-Glu-Phe-Ile-Ala-Trp-Leu-Val-Arg-Gly-Arg-Gly-OH (SEQ ID No. 1). Liraglutide, developed by Novo Nordisk, Denmark, is a glucagon-like peptide-1 (GLP-1) receptor agonist, which has favorable hypoglycemic effect as a formulation for subcutaneous injection.

Liraglutide from Novo Nordisk is prepared primarily by biological methods, such as genetic engineering, etc. Such methods, however, are not suitable for large-scale production of liraglutide, due to its complex techniques and high cost. Solid-liquid phase synthesis of liraglutide has been described in U.S. Pat. Nos. 6,268,343B1 and 6,458,924B2, in which reverse-phase HPLC is required for the purification of the intermediate GLP-1(7-37)-OH, followed by reaction with Nα-alkanoyl-Glu(ONSu)-OtBu in liquid phase. In such process, the N-terminal of GLP-1(7-37)-OH is not protected and protective groups for the side chains are all removed, leading to generation of a great amount of impurities, difficulties in purification and complicated operation steps. The synthesis methods of liraglutide in the prior art have disadvantages, such as, complicated operation process requiring two purification steps, long synthesis cycle, large amount of waste liquid which is not environmentally friendly, a great amount of acetonitrile required, high cost and unsuitability in large-scale production.

SUMMARY OF THE INVENTION

A method for solid phase synthesis of liraglutide is provided in the present invention, in order to solve existing problems in the prior art.

A method for solid phase synthesis of liraglutide, comprising the following steps:

in the presence of an activating agent system, Fmoc-Gly-resin is obtained by coupling N-terminal Fmoc-protected glycine (Fmoc-Gly-OH) to a resin solid-phase support;

by solid-phase synthesis, amino acids with N-terminal Fmoc protection and side chain protection are sequentially coupled based on the sequence of peptide backbone of liraglutide, wherein Fmoc-Lys(Alloc)-OH is employed for lysine;

the protective group Alloc for side chain of lysine is removed;

by solid phase synthesis, palmitoyl-Glu-OtBu is coupled to the side chain of lysine;

crude liraglutide is obtained by cleavage, and removal of the protective groups and the resin;

liraglutide is finally obtained by purification and lyophilizing.

By the above-mentioned technical solution, the preparation of liraglutide by solid phase synthesis has advantages, such as, simple operation steps, short synthesis cycle, low cost, less waste liquid produced, less by-product, high yield and suitability for large-scale production of liraglutide.

For further improving the present invention, in said step A), 2-CTC resin is employed as the resin solid phase support, and the activating agent system is selected from the group consisting of DIEA, TMP or NMM(N-methylmorpholine), and said Fmoc-Gly-resin is the Fmoc-Gly-CTC resin with a substitution degree in the range from 0.15 to 0.28 mmol/g.

For further improving the present invention, in said step A), Wang resin is employed as the resin solid phase support, and the activating agent system consists of DIC, HOBt and DMAP (dimethylaminopyridine), and said Fmoc-Gly-resin is the Fmoc-Gly-Wang resin with a substitution degree in the range from 0.12 to 0.24 mmol/g.

For further improving the present invention, said step B) comprises the following steps:

B1) H-Gly-resin is obtained by removing the Fmoc protective group from the Fmoc-Gly-resin using DBLK, wherein said DBLK consists of piperidine and DMF in a volume ratio of 1:4;

B2) in the presence of a coupling agent system, Fmoc-Arg(Pbf)-Gly-resin is obtained by coupling the Fmoc-protected and side-chain protected arginine to the H-Gly-resin;

B3) by repeating steps B1 and B2, amino acids are coupled sequentially based on the peptide sequence of the backbone of liraglutide.

When amino acids are coupled, the side-chain protection for tryptophan is achieved by a Boc-protective group; the side-chain protection for glutamic acid is achieved by an OtBu-protective group; the side-chain protection for lysine is achieved by an Alloc-protective group; the side-chain protection for glutamine is achieved by a Trt-protective group; the side-chain protection for tyrosine is achieved by a tBu-protective group; the side-chain protection for serine is achieved by a Trt- or tBu-protective group. For the purpose of ensuring the coupling efficiency to the resin and the final product yield, different protective groups including Trt or tBu are employed for serine. The side-chain protection for aspartate is achieved by an OtBu-protective group. The side-chain protection for threonine is achieved by a tBu-protective group. For histidine, the side-chain is protected by a Trt-protective group, and the N-terminal is protected by a Boc-protective group.

For further improving the present invention, said coupling agent system comprises condensation agent and reaction solvent, and said condensation agent is selected from the group consisting of DIC/HOBt, PyBOP/HOBt/DIEA or HATU/HOAt/DIEA; and said reaction solvent is selected from the group consisting of DMF, DCM, NMP, DMSO or any combination thereof.

For further improving the present invention, in said step c), the protective group Alloc for the side-chain of lysine is removed by using 0.1-0.4 fold of synthesis-scale amount of Pd(PPh$_3$)$_4$ and 10-30 folds of synthesis-scale amount of phenyl silane under the solid phase condition for 10-65 min.

In said step D), the side-chain lysine can be coupled directly to palmitoyl-Glu-OtBu, alternatively, coupled to Fmoc-Glu-OtBu initially, followed by removal of Fmoc, and then coupled to palmitoyl chloride.

In side step E), "peptide cleavage reaction", generally used in the art, is performed to remove protective groups and resin, thus crude liraglutide is obtained.

For further improving the present invention, in said step F), the purification is performed by reverse-phase high performance liquid chromatography using reverse-phase C8 column with column temperature in the range from 40 to 50° C.

Compared to the prior art, the benefit of the present invention is to provide a solid-phase synthesis method for preparing liraglutide, which has advantages, such as, simple operation steps, short synthesis cycle, low cost, less waste liquid produced, easy post-processing, less by-product, high yield and suitable for large-scale production of liraglutide.

BRIEF DESCRIPTION OF THE DRAWINGS

FIG. 1 is a flow chart of the solid phase synthesis process for liraglutide comprising SEQ ID NO. 1, according to the present invention.

DESCRIPTION OF THE SPECIFIC EMBODIMENTS

A method for solid phase synthesis of liraglutide is disclosed by the present invention, which can be implemented by those skilled in the art by properly modifying the processing parameters with reference to the contents herein. Particularly, it should be noted that all similar replacements and modifications are apparent to those skilled in the art, all of which are regarded to be covered by the present invention. The method of the present invention will be described by preferred examples, and it is apparent that modification, or proper change and the combination thereof can be made to the method and the application described herein by those skilled in the art, without departing from the content, spirit and scope of the invention, in order to achieve and apply the techniques disclosed in the present invention.

The present invention will be further illustrated with reference to the specific examples below, in order to render the technical solutions of the present invention better understood by those skilled in the art.

Both Wang resin and CTC resin are purchased from Tianjin Nankai Hecheng Science & Technology Co., Ltd, and various protected amino acids are purchased from GL Biochem Company. Abbreviations used in the specification and claims are listed in the table below:

| | |
|---|---|
| Fmoc | 9-fluorenylmethyloxycarbonyl |
| HBTU | O-Benzotriazole-N,N,N',N'-tetramethyluronium hexafluorophosphate |
| HATU | O-(7-Aza-benzotriazole-1-oxy)-N,N,N',N'-tetramethyluronium hexafluorophosphate |
| PyBOP | (Benzotriazol-1-oxy)-tripyrrolidinophosphonium hexafluorophosphate. |
| DIC | Diisopropylcarbodiimide |
| HOBt | 1-hydroxybenzotriazole |
| HOAt | 1-hydroxy-7-azabenzotriazole |
| DIEA | N,N-diisopropylethylamine |
| TMP | 2,4,6-trimethylpyridine |
| Pbf | 2,2,4,6,7-pentamethyldihydrobenzofuran-5-sulfonyl |
| Trt | Trityl |
| tBU | Tert-butyl |
| DMF | N,N-dimethyl formamide |
| DCM | Dichloromethane |
| 2-CTC | 2-chlorotrityl resin |
| TFA | Trifluoroacetic acid |
| Alloc | Allyloxycarbonyl |
| NMP | N-methyl pyrrolidone |
| DMSO | Dimethyl sulfoxide |
| Palmitoyl | Palmitoyl |
| EDT | Ethanedithiol |
| Pd(PPh$_3$)$_4$ | Tetrakis(triphenylphosphine)palladium |
| PhSiH3 | Phenylsilane |

EXAMPLE 1

Synthesis of Fmoc-Gly-CTC Resin with a Substitution Degree of 0.15 mmol/g 20 g 2-CTC resin with a substitution degree of 0.5 mmol/g was weighed and added to the solid-phase reaction column. Subsequently, the resin was washed twice with DMF, and swollen in DMF for 30 min. 4.3 g Fmoc-Gly-OH was then dissolved in DMF and activated by adding 4.78 mL DIEA under ice water bath before loaded to the above-mentioned reaction column filled with resin. After reacting for 2 h, 8 mL absolute methanol was added to block for 1 h. The resin was washed for 3 times by each of DMF and DCM, and blocked for 30 min by absolute methanol. After the resin was shrunk by methanol, methanol was drawn to dryness to obtain Fmoc-Gly-CTC resin with a detected substitution degree of 0.15 mmol/g.

EXAMPLE 2

Synthesis of Fmoc-Gly-CTC Resin with a Substitution Degree of 0.28 mmol/g 11.1 g 2-CTC resin with a substitution degree of 0.9 mmol/g was weighed and added to the solid-phase reaction column. Subsequently, the resin was washed twice with DMF, and swollen in DMF for 30 min. 5.78 g Fmoc-Gly-OH was then dissolved in DMF and activated by adding 6.94 mL DIEA under ice water bath before loaded to the above-mentioned reaction column loaded with resin. After reacting for 2 h, 8 mL absolute methanol was added to block for 1 h. The resin was washed by DMF and DCM for 3 times respectively, and blocked for 30 min by absolute methanol. After the resin was shrunk by methanol, methanol was drawn to dryness to obtain Fmoc-Gly-CTC resin with a detected substitution degree of 0.15 mmol/g.

EXAMPLE 3

Synthesis of Fmoc-Gly-Wang Resin with a Substitution Degree of 0.24 mmol/g 13.1 g Wang resin with a substitution degree of 0.75 mmol/g was weighed and added to the solid-phase reaction column. Subsequently, the resin was washed twice with DMF, and swollen in DMF for 30 min. 4.3 g Fmoc-Gly-OH and 3.78 g HOBt was then dissolved in DMF and activated by adding 2.84 mL DIC under ice water bath before loaded to the above-mentioned reaction column loaded with resin. After 5 min, 268 mg DMAP was added and reacted for 2 h. Subsequently, the resin was washed by DMF and DCM for 3 times respectively, and blocked by 100 mL acetic anhydride/pyridine over night. After the resin was shrunk by methanol, methanol was drawn to dryness to obtain Fmoc-Gly-Wang resin with a detected substitution degree of 0.24 mmol/g.

EXAMPLE 4

Synthesis of Fmoc-Gly-Wang Resin with a Substitution Degree of 0.12 mmol/g 9.2 g Wang resin with a substitution degree of 1.1 mmol/g was weighed and added to the solid-phase reaction column. Subsequently, the resin was washed twice using DMF, and swollen in DMF for 30 min. 2.9 g Fmoc-Gly-OH and 1.78 g HOBt was then dissolved in DMF and activated by adding 1.65 mL DIC under ice water bath before loaded to the above-mentioned reaction column loaded with resin. After 5 min, 137 mg DMAP was added and reacted for 2 h. Subsequently, the resin was washed by DMF and DCM for 3 times respectively, and blocked by 80 mL acetic anhydride/pyridine over night. After the resin was shrunk by methanol, methanol was drawn to dryness to obtain Fmoc-Gly-Wang resin with a detected substitution degree of 0.12 mmol/g.

EXAMPLE 5

Preparation of Linear Liraglutide CTC Resin 10 g Fmoc-Gly-CTC resin with a substitution degree of 0.15 mmol/g was weighed and added to the solid-phase reaction column. Subsequently, the Fmoc-Gly-CTC resin was washed twice using DMF, and swollen in DMF for 30 min. Fmoc protection was removed by 20% DBLK, and the resin was then washed for 4 times with DMF and twice by DCM. The resin was tested by ninhydrin test, in which the removal of Fmoc was indicated by the appearance of color of the resin. 3.89 g Fmoc-Arg(Pbf)-OH (6.0 mmol), 0.97 g HOBt (7.2 mmol), 0.91 g DIC (7.2 mmol) were dissolved in a mixed solution of DCM and DMF in a volume ratio of 1:1, loaded to the solid-phase reaction column and reacted at room temperature for 2 h. The endpoint of the reaction was determined by ninhydrin test, in which the colorless and transparent resin indicated a complete reaction; while a color developed by the resin indicated an incomplete reaction, for which another 1 h reaction was required. Such criteria were applied to the endpoint determination by ninhydrin test herein below. The above Fmoc de-protection step and corresponding amino acid coupling step were repeated, and based on the sequence of peptide backbone of liraglutide, Fmoc-Gly-OH, Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Alloc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(Trt)-OH, Fmoc-Ser(Trt)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH and Boc-His(Trt)-OH were sequentially coupled. In the reaction process, PyBOP/HOBt/DIEA system was employed for Fmoc-Ile-OH, and the reaction solvent was the mixed solution of DMSO and DMF in a volume ratio of 1:4; PyBOP/HOBt/DIEA system was employed for Fmoc-Ala-OH, and the reaction solvent was DCM; PyBOP/HOBt/DIEA system was employed for Fmoc-Gln(Trt)-OH, and the reaction solvent was the mixed solution of DMSO and NMP in a volume ratio of 1:4; HATU/HOAt/TMP system was employed for Fmoc-Ser(Trt)-OH and Fmoc-Ser(tBu)-OH, and the reaction solvent was NMP; in order to ensure the coupling efficiency to the resin and the final product yield, different protective groups, including Trt and tBu, were employed for serine. The linear liraglutide CTC resin was washed for 3 times by DMF and for 5 times by DCM for subsequent synthesis reaction.

EXAMPLE

Preparation of Linear Liraglutide Wang Resin 12.5 g Fmoc-Gly-Wang resin with a substitution degree of 0.12 mmol/g was weighed and added to the reactor. Subsequently, the Fmoc-Gly-Wang resin was washed twice using DMF, and swollen in DMF for 30 min. Fmoc protection was removed by 20% DBLK, and the resin was then washed for 4 times using DMF and twice by DCM. The resin was tested by ninhydrin test, in which the removal of Fmoc was indicated by the appearance of color of the resin. 3.89 g Fmoc-Arg(Pbf)-OH (6.0 mmol), 0.97 g HOBt (7.2 mmol), 0.91 g DIC (7.2 mmol) were dissolved in a mixed solution of DCM and DMF in a volume ratio of 1:1, loaded to the solid-phase reaction column and reacted at room temperature for 2 h. The reaction endpoint was determined by ninhydrin test. The above Fmoc de-protection step and corresponding amino acid coupling step were repeated, and based on the sequence of peptide backbone of liraglutide, Fmoc-Gly-OH, Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Alloc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(Trt)-OH, Fmoc-Ser(Trt)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH and Boc-His(Trt)-OH were sequentially coupled. In the reaction process, PyBOP/HOBt/DIEA system was employed for Fmoc-Ile-OH, and the reaction solvent was a mixed solution of DMSO and DMF in a volume ratio of 1:4; PyBOP/HOBt/DIEA system was employed for Fmoc-Ala-OH, and the reaction solvent was DCM; PyBOP/HOBt/DIEA system was employed for Fmoc-Gln(Trt)-OH, and the reaction solvent was a mixed solution of DMSO and NMP in a volume ratio of 1:4; HATU/HOAt/TMP system was employed for Fmoc-Ser(Trt)-OH and Fmoc-Ser(tBu)-OH, and the reaction solvent was NMP. In order to ensure the coupling efficiency to the resin and the final product yield, different protective groups, including Trt and tBu, were employed for serine. The resin was washed for 3 times by DMF and 5 times by DCM for the next reaction.

EXAMPLE 7

Synthesis of N$^\alpha$-Palmitoyl-Glu-OtBu

H-Glu-OtBu (20.3 g, 100 mmol) was weighed and added to a three-neck bottle containing 200 mL dichloromethane. The mixture was cooled to 5° C. in an ice water bath, and then 5.7 mL (50 mmol) triethylamine was added. After 20 min, 32.88 g (120 mmol) palmitoyl chloride was dropwise added slowly over a period of 30 min. After the addition was finished, the system was warmed up naturally to room temperature and reacted for another 2 h. The complete reaction of the raw materials was monitored by thin-layer chromatography (TLC). The reaction solution was sequentially extracted by 100 mL saturated $NaHCO_3$ twice, 100 mL de-ionized water twice, and 100 mL saturated saline solution for 3 times, and then the aqueous phase was discarded. The organic phase was dried with anhydrous sodium sulfate for 30 min. DCM was removed by a rotary evaporator to obtain an oil product. 200 mL mixed solution of ethyl acetate/petroleum ether was added to the oil product and placed in a freezer for 2 h. Subsequently, white solid appeared. The white solid was re-crystallized once in the same manner. After filtration and vacuum drying, 38.74 g white solid was obtained with a yield of 87.72%.

EXAMPLE 8

Synthesis of Liraglutide CTC Resin

To the linear liraglutide CTC resin obtained in Example 5, was added 30 mL dichloromethane, followed by 2.21 mL phenyl silane. After reaction was performed for 3 min, 467 mg Pd(PPh$_3$)$_4$ was added, and the reaction was performed at room temperature for 45 min. The reaction solution was sucked and discarded, and the appearance of color of the resin was detected by ninhydrin test. A color developed by the resin indicated removal of Fmoc.

3.18 g Fmoc-Glu-OtBu, 3.9 g PyBOP, 1.22 g HOBt were weighed and dissolved in 25 mL dichloromethane. The system was activated under an ice water bath for 3 min by adding 2.7 mL DIEA and loaded to the reaction column for 2 h reaction. The endpoint of reaction was determined by ninhydrin test. After the reaction was finished, Fmoc was removed, and the resin was washed by DMF for 6 times. Subsequently, 1.22 g palmitoyl chloride and 2.1 mL DIEA were added, and reacted at room temperature for 2 h. The reaction endpoint was determined by ninhydrin test. After the reaction was finished, the resin was shrunk in methanol, and dried under vacuum over night. After weighing, 16.5 g liraglutide CTC resin was obtained (weight increase rate of resin was 81.1%).

EXAMPLE 9

Synthesis of Liraglutide Wang Resin

To the linear liraglutide Wang resin obtained in Example 6, was added 30 mL dichloromethane, followed by 2.21 mL phenyl silane. After reacted for 3 min, 467 mg Pd(PPh$_3$)$_4$ was added, and reacted at room temperature for 45 min. The reaction solution was sucked and discarded, and the appearance of color of the resin was detected by ninhydrin test. A color developed by the resin indicated removal of Fmoc.

Method 1: 2.18 g Palmitoyl-Glu-OtBu, 3.9 g PyBOP, 1.22 g HOBt were weighed and dissolved in 25 mL NMP. The system was activated under an ice water bath for 3 min by adding 2.7 mL DIEA and loaded to the reaction column for 2 h reaction. The endpoint of reaction was determined by ninhydrin test. After the reaction was finished, the resin was shrunk in methanol, and dried under vacuum over night. After weighing, 20.1 g liraglutide Wang resin was obtained (weight increase rate of resin was 94.7%).

Method 2: 3.18 g Fmoc-Glu-OtBu, 3.9 g PyBOP, 1.22 g HOBt were weighed and dissolved in 25 mL dichloromethane. The system was activated under an ice water bath for 3 min by adding 2.7 mL DIEA and loaded to the reaction column for 2 h reaction. The endpoint of reaction was determined by ninhydrin test. After the reaction was finished, Fmoc was removed, and the resin was washed by DMF for 6 times. Subsequently, 1.22 g palmitoyl chloride and 2.1 mL DIEA were added, and the reaction was performed at room temperature for 2 h. The reaction endpoint was determined by ninhydrin test. After the reaction was finished, the resin was shrunk in methanol, and dried under vacuum over night. After weighing, 19.8 g liraglutide resin was obtained (weight increase rate of resin was 91.1%).

EXAMPLE 10

Large-scale Preparation of Liraglutide Wang Resin

By reference to Example 6, 833.3 g Fmoc-Gly-Wang resin with a substitution degree of 0.12 mmol/g was weighed and added to the reactor. Subsequently, the resin was washed twice using DMF, and swollen in DMF for 30 min. Fmoc protection was removed by 20% DBLK, and the resin was then washed for 4 times using DMF and twice by DCM. 259.2 g Fmoc-Arg(Pbf)-OH (400 mmol), 64.8 g HOBt (480 mmol), 60.5 g DIC (480 mmol) were dissolved in a mixed solution of DCM and DMF in a volume ratio of 1:1, loaded to the solid-phase reaction column and reacted at room temperature for 2 h. The reaction endpoint was determined by ninhydrin test.

The above Fmoc de-protection step and corresponding amino acid coupling step were repeated, and based on the sequence of peptide backbone of liraglutide, Fmoc-Gly-OH, Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Alloc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(Trt)-OH, Fmoc-Ser(Trt)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(Trt)-OH were sequentially coupled. The liraglutide Wang resin was washed for 3 times by DMF and for 5 times by DCM.

6500 mL dichloromethane was added to the linear liraglutide Wang resin obtained above, followed by 147.3 mL phenyl silane. After the reaction was performed for 3 min, 31.3 g Pd(PPh$_3$)$_4$ was added. The reaction was performed at room temperature for 45 min. The reaction solution was sucked and discarded, and the appearance of color of the resin was detected by ninhydrin test. A color developed by the resin indicated removal of Fmoc. 145.3 g Palmitoyl-Glu-OtBu, 260 g PyBOP, 81.0 g HOBt were weighed and dissolved in 4.5 L NMP. The system was activated under an ice water bath for 3 min by adding 174.3 mL DIEA, and loaded to the reaction column for 2 hours' reaction. The endpoint of reaction was determined by ninhydrin test. After the reaction was finished, the resin was shrunk in methanol, and dried under vacuum over night. After weighing, 1335.5 g liraglutide resin was obtained (weight increase rate of resin was 94.1%).

EXAMPLE 11

Preparation of Crude Liraglutide 130 g completely protected liraglutide CTC resin or liraglutide Wang resin was weighed and added to a 2 L reactor. 1.3 L cleavage reagent was formulated in a volume ratio of TFA:thioanisole:anisole:EDT=90:5:3:2. The cleavage reagent was poured into the liraglutide CTC resin or liraglutide Wang resin, and the reaction was performed at room temperature for 2.5 h. After the reaction was finished, the resin was filtered out and the filtrate was collected. The resin was washed by a small amount of TFA. The filtrates were combined and added to 11 L anhydrous ethyl ether. After precipitation and centrifugation, the pellet was washed by anhydrous ethyl ether and dried under vacuum to give 42.72 g crude liraglutide with a yield of 80.5%. MALDI-TOF: (M+H)$^+$=3752.1.

EXAMPLE 12

Preparation of Polished Liraglutide Hydrochloride 42.7 g crude liraglutide was weighed and dissolved in 1000 mL mixed solvent of 25% acetonitrile+25% DMSO+50% water. The crude liraglutide was purified by Waters 2545 RP-HPLC system equipped with a 50×250 mm reverse-phase C8 column at column temperature of 45° C. using routine 0.1% TFA/acetonitrile as mobile phase at detection wavelength of 214 nm. The target fraction was collected to give the purified peptide with a purity greater than 98.5%. In Waters 2545 RP-HPLC system equipped with 50×250 mm reverse-phase C8 column, the purified peptide solution was converted into salt using 0.1% hydrochloric acid/acetonitrile as mobile phase. The target fraction was collected and concentrated by rotary evaporation. After lyophilization, 6.75 g purified liraglutide hydrochloride was obtained with HPLC purity of 99.1%, purification yield of 52.7% and overall yield of 15.32%.

EXAMPLE 13

Preparation of Purified Liraglutide Acetate 42.7 g crude liraglutide was weighed and dissolved in 1000 mL mixed solvent of 25% acetonitrile+25% DMSO+50% water. The crude liraglutide was purified by Waters 2545 RP-HPLC system equipped with a 50×250 mm reverse-phase C8 column at column temperature of 45° C. using routine 0.1% TFA/acetonitrile as mobile phase at detection wavelength of 214 nm. The target fraction was collected to give the purified peptide with a purity greater than 98.5%. In Waters 2545 RP-HPLC system equipped with 50×250 mm reverse-phase C8 column, the purified peptide solution was converted into salt using 0.2% acetic acid/acetonitrile as mobile phase. The target fraction was collected and concentrated by rotary evaporation. After lyophilization, 6.83 g purified liraglutide acetate was obtained with HPLC purity of 99.23%, purification yield of 54.7% and overall yield of 15.68%.

EXAMPLE 14

Preparation of Purified Liraglutide Trifluoroacetate 42.7 g crude liraglutide was weighed and dissolved in 1000 mL mixed solvent of 25% acetonitrile+25% DMSO+50% water. The crude liraglutide was purified by Waters 2545 RP-HPLC system equipped with a 50×250 mm reverse-phase C8 column at column temperature of 45° C. using routine 0.1% TFA/acetonitrile as mobile phase at detection wavelength of 214 nm. The target fraction was collected to give the purified peptide with a purity greater than 98.5%. In Waters 2545 RP-HPLC system equipped with 50×250 mm reverse-phase C8 column, the purified peptide solution was converted into salt using 0.1% trifluoroacetic acid/acetonitrile as mobile phase. The target fraction was collected and concentrated by rotary evaporation. After lyophilization, 6.88 g purified liraglutide acetate was obtained with HPLC purity of 99.17%, purification yield of 55.2% and overall yield of 15.87%.

The above contents are further description of the present invention by reference to specific preferable embodiments, and it should not be deemed that specific practice of the present invention is limited to such description. For a person skilled in the art, some simple deduction and substitutions can be made without departing from the concept of the present invention, and should be deemed to be included in the protection scope of the present invention.

The invention claimed is:

1. A method for solid phase synthesis of liraglutide, which is characterized in that the method comprises the following steps:
   A) in the presence of an activating agent system, Fmoc-Gly-resin is obtained by coupling N-terminal Fmoc-protected glycine (Fmoc-Gly-OH) to a resin solid-phase support;
   B) by solid-phase synthesis, amino acids with N-terminal Fmoc protection and side chain protection are sequentially coupled based on the sequence of peptide backbone of liraglutide, wherein Fmoc-Lys(Alloc)-OH is employed for lysine;
   C) the protective group Alloc for the side chain of lysine is removed;
   D) by solid phase synthesis, palmitoyl-Glu-OtBu is coupled to the side chain of lysine;
   E) crude liraglutide is obtained by cleavage, and removal of the protective groups and the resin;
   F) liraglutide is finally obtained by purification and lyophilizing,
   wherein the purification is performed by a reverse-phase high performance liquid chromatography using a reverse-phase C8 column with a column temperature in the range from 40 to 50° C.

2. The method for solid phase synthesis of liraglutide according to claim 1, which is characterized in that in said step A), 2-CTC resin is employed as the resin solid phase support, and the activating agent system is selected from the group consisting of DIEA, TMP and NMM (N-methylmorpholine), and said Fmoc-Gly-resin is an Fmoc-Gly-CTC resin with a substitution degree in the range from 0.15 to 0.28 mmol/g.

3. The method for solid phase synthesis of liraglutide according to claim 1, which is characterized in that in said step A), Wang resin is employed as the resin solid phase support, and the activating agent system consists of DIC, HOBt and DMAP (dimethylaminopyridine), and said Fmoc-Gly-resin is an Fmoc-Gly-Wang resin with a substitution degree in the range from 0.12 to 0.24 mmol/g.

4. The method for solid phase synthesis of liraglutide according to claim 1, which is characterized in that said step B) comprises the following steps:
   B1) H-Gly-resin is obtained by removing the Fmoc protective group from the Fmoc-Gly-resin using DBLK, wherein said DBLK consists of piperidine and DMF in a volume ratio of 1:4;

---

SEQUENCE LISTING

```
<160> NUMBER OF SEQ ID NOS: 1

<210> SEQ ID NO 1
<211> LENGTH: 31
<212> TYPE: PRT
<213> ORGANISM: Artificial Sequence
<220> FEATURE:
<223> OTHER INFORMATION: a known glucogon-like peptide-1 receptor
      agonist

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

B2) in the presence of a coupling agent system, Fmoc-Arg(Pbf)-Gly-resin is obtained by coupling the Fmoc-protected and side-chain protected arginine to the H-Gly-resin;

B3) by repeating steps B1 and B2, amino acids are coupled sequentially based on the sequence of the peptide backbone of liraglutide.

5. The method for solid phase synthesis of liraglutide according to claim 4, which is characterized in that, said coupling agent system comprises a condensation agent and a reaction solvent, and said condensation agent is selected from the group consisting of DIC/HOBt, PyBOP/HOBt/DIEA and HATU/HOAt/DIEA; and said reaction solvent is selected from the group consisting of DMF, DCM, NMP, DMSO and any combination thereof.

6. The method for solid phase synthesis of liraglutide according to claim 1, which is characterized in that, in said step C), the protective group Alloc for the side chain of lysine is removed by using 0.1-0.4 fold of $Pd(PPh_3)_4$ and 10-30 folds of phenyl silane under solid phase conditions for 10-65 min.

* * * * *